United States Patent [19]
Atkinson

[11] Patent Number: 5,239,862
[45] Date of Patent: Aug. 31, 1993

[54] APPARATUS AND METHOD FOR MEASURING FLUID PROPERTIES

[75] Inventor: David I. H. Atkinson, Farnham, England

[73] Assignee: Schlumberger Technology Corporation, Houston, Tex.

[21] Appl. No.: 762,291

[22] Filed: Sep. 19, 1991

[30] Foreign Application Priority Data

Sep. 24, 1990 [GB] United Kingdom ............... 9020759

[51] Int. Cl.$^5$ ................... G01N 33/00; G01N 27/06; G01D 18/00
[52] U.S. Cl. .................. 73/64.44; 73/1 R; 73/64.56; 324/601; 364/509; 364/571.02
[58] Field of Search ............ 73/1 R, 1 G, 3, 23.21, 73/61.44, 61.45, 61.59, 64.44, 64.56, 863.31, 4 R; 324/601, 693, 720; 364/571.01–571.08, 509

[56] References Cited

U.S. PATENT DOCUMENTS

| | | | |
|---|---|---|---|
| 3,430,483 | 3/1969 | Clawson et al. | 73/64.44 X |
| 3,528,440 | 9/1970 | Plucker, III | 73/64.44 X |
| 3,721,121 | 3/1973 | Fierfort | 73/155 |
| 3,924,445 | 12/1975 | Konomi et al. | 73/3 |
| 4,713,618 | 12/1987 | Carlson et al. | 73/1 R X |
| 4,713,772 | 12/1987 | Carlson | 73/863.31 X |
| 4,856,344 | 8/1989 | Hunt | 73/861.04 |
| 4,974,452 | 12/1990 | Hunt et al. | 73/861.64 |

FOREIGN PATENT DOCUMENTS 0208045 1/1987 European Pat. Off. .
1151568 5/1969 United Kingdom .

Primary Examiner—Tom Noland
Attorney, Agent, or Firm—John J. Ryberg; Wayne I. Kanak

[57] ABSTRACT

A meter for measuring a material property of a fluid comprises a pair of parallel passage (6, 8) arranged in a line (2). The passages (6, 8) are alternately isolated by valves (12) thereby trapping a portion of the fluid. Measurements made at a measuring station (10) either during closure of the valves (12) and/or during gravitational separation of the multi-phase fluid enable a calibration of the meter to be made.

16 Claims, 7 Drawing Sheets

ON-LINE CALIBRATION FOR 2-PHASE SYSTEM

MEASUREMENT (e.g., IMPEDANCE)

CALIBRATION (ELIMINATE t)

APPARATUS AND METHOD FOR MEASURING FLUID PROPERTIES

BACKGROUND OF THE INVENTION

1. Field of the Invention

This invention relates to an apparatus and method for measuring properties of fluids and in particular to meters which can be calibrated "in line" in accordance with the present invention and the methods by which they are calibrated.

Multi-phase fluids are frequently encountered in the production of oil. Typically the fluid emerging from an oil reservoir will comprise a mixture of oil, water and gas. A detailed knowledge of the physical properties of the fluid mixture as it emerges from an oil reservoir is extremely useful and thus enabling production from the reservoir to be optimised.

One method of determining the physical properties is to provide appropriate meters in line with the pipe in which the oil is produced. Each meter would be calibrated in a laboratory, before insertion in the line. The problem with this calibration is that in a laboratory it would be subject to different environmental conditions, such as electrical interference patterns, than it would experience in situ. This problem would be particularly apparent with, for example, an impedance meter which would be susceptible to stray capactiances in the calibration apparatus.

The other problem in performing this laboratory calibration is choosing the correct range over which to calibrate, because it is difficult to predict the field values. In addition, small variations in the composition of the fluid used to calibrate the meter can significantly effect the calibration for example, properties such as impedance are very sensitive to the salt concentration in any water phase in the fluid. Small variations in the salt concentration can lead to large variations in the unit impedance of the fluid. Thus it is necessary to make calibrations for a large number of salt concentrations to obtain an accurate calibration and operation in the field requires the concentration of salt in the measurement fluid to be known.

It is well known that it is difficult in practice to take a sample of a multi-phase fluid which is representative of the concentrations of the fluid phases. For example, when a sample of fluid is taken in the wellbore of an oil well at certain temperature and pressure downhole conditions, the sample is then sent to a laboratory where it is recombined to down hole conditions. However, there is no knowledge of the way in which the phases changed on the way to the surface and it is possible that extra water or gas could have been combined with the fluid on the way up. It is not possible to recalibrate the meter without moving it from its position in line and returning it to the laboratory.

2. Description of the Related Art

It has been proposed to calibrate fluid flow meters by diverting flow through a calibration zone in the meter. GB 1,151,568 and EP 0,208,045 both describe systems for calibrating gas flow meters. GB 1,151,568 describes a system in which gas flow can be diverted into a calibration zone by operation of valves such that the flow of gas into the zone of known volume can be measured. EP 0,208,045 effects calibration by diverting flow into a further pipeline having an instrumented bypass line to allow calibration of the flow through the further pipeline.

U.S. Pat. No. 3,721,121 describes an apparatus for investigating multi-phase fluids, comprising a chamber for trapping a fluid sample and means for detecting the level of the interface between the two phases after separation. The trapped sample must be representative of the multi-phase fluid and no measurement is made during separation of the phases.

SUMMARY OF THE INVENTION

One object of the present invention is to provide an apparatus for measuring a property of a fluid, typically comprising a mixture of immiscible fluids, which can be calibrated "in line" and to provide a method for calibration of a meter.

In accordance with a first aspect of the present invention, there is provided an apparatus for measuring at least one property of a flowing fluid comprising a pair of substantially parallel passages through which said flowing fluid is directed, a transducer being connected to a measurement point in each passage to measure said at least one property, data from the transducer being used to calibrate measurements made with the apparatus, characterised in that means are provided to isolate one of said passages such that fluid flow is prevented therein and means are provided to calculate, from the response of the transducer therein, calibration data for the transducer measuring the flowing fluid.

The present invention also provides a method for measuring at least one property of a flowing fluid comprising directing the fluid into two substantially parallel passages and obtaining calibration data for the measurement from measurements made in one of the passages, characterised by isolating one passage so as to prevent flow therein and measuring said property in the isolated passage and calculating therefrom calibration data for the corresponding flowing measurement.

Preferably the isolating means allows each passage to be alternately isolated or flowing. It is also preferred that measurements are made in the isolated passage from after isolation until any phases present in the fluid are separated.

Where the fluid comprises a mixture of two or three phases, transducers are typically provided to make measurements on the pure phase after fluid separation.

BRIEF DESCRIPTION OF THE DRAWINGS

The invention will now be described in more detail by way of example with reference to the drawings in which.

DESCRIPTION OF THE PREFERRED EMBODIMENTS

The current invention operates by isolating a sample of the fluid at line conditions and allowing it to separate out under gravity. A property of the fluid is measured at one or more points by an appropriate transducer and monitored against time as the fluid phases separate. Clearly at a given position the concentration of phases will vary with time. The respective concentrations of each phase in the sample can be determined once separation is complete and a mathematical model of the separation against time determined. The measured parameter and the separation model are then combined to eliminate the time variable thus producing a calibration of the measurement against concentration. The time variable is thus used as a "dummy" variable to link the measurement to concentration. The variation of concentration with time is relatively easy to model for gravitational separation and thus no complex computation is required to produce the calibration. Furthermore the method does not require the sample to be representative of the exact concentrations of the phases in the flowing fluid and does not require any prior knowledge of the measured parameter as a function of the pure phases and concentrations thereof.

One parameter that can be measured is the complex impedance of the fluid. The object of measuring the complex impedance is to determine the concentration of each of the phases, in a mixture of the phases.

The relationship between concentration and the complex impedance of a three phase fluid is explained below:

Let $C_{(i)}$, be the concentration of each phase such that for a three phase mixture:

$$C_{(1)} + C_{(2)} + C_{(3)} = 1$$

The complex impedance z, of a mixture of these phases has a real part $Z_r$ and an imaginary part $Z_i$ where;

$$Z_r = F[C_{(i)}, e_{(i)}, r_{(i)}]$$

$$Z_i = G[C_{(i)}, e_{(i)}, r_{(i)}]$$

If $r_{(i)}$ and $e_{(i)}$, the conductivity and relative permittivity of the pure phases, are known and the functions F and G are known then the concentrations of the pure phases $C_{(i)}$ can be determined simply from measurements of $Z_r$ and $Z_i$ of the mixture.

Figure 1A:
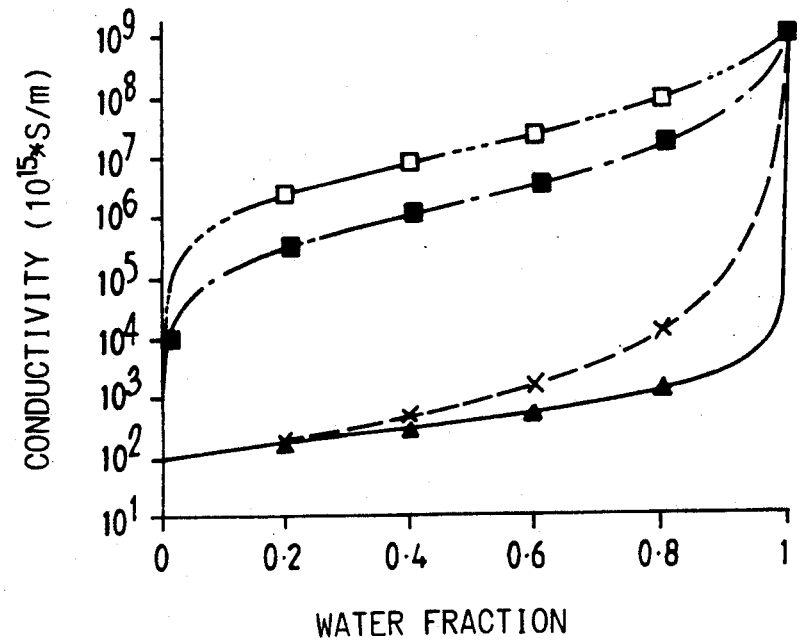
FIGS. 1a) and b) show various theoretical models of the conductivity and permittivity for water/oil concentration.
Figure 1B:
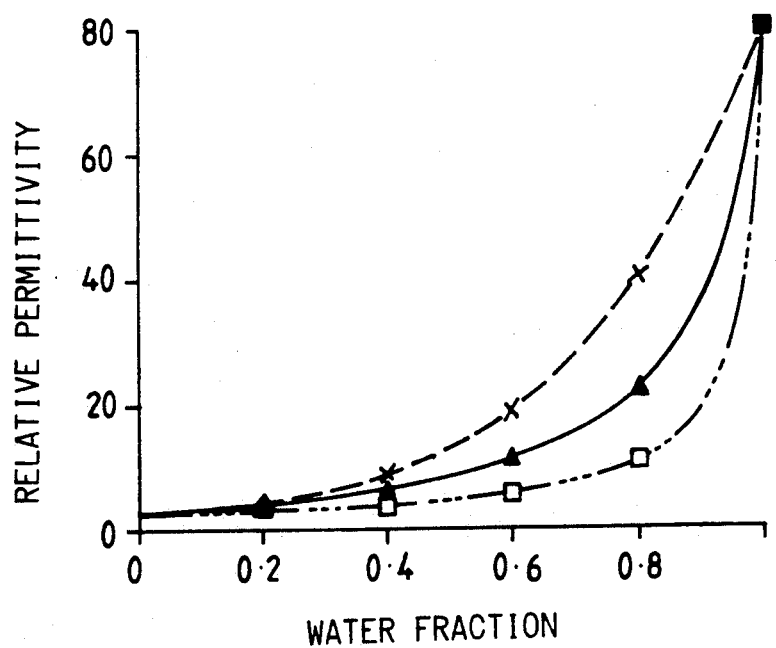

Theoretical models of conductivity and relative permittivity as a function of water fraction in a mixture of crude oil and sea water have been made in the past. Examples of these are shown in FIG. 1. The two graphs shows the variation of conductivity in FIG. 1(a), and relative permittivity in FIG. 1(b), against water fraction computed from different models (in FIG. 1(b), two models give the same results). It can be seen clearly that there is considerable variation between each of the models. Thus it is not possible to provide an accurate estimate of F and G from these models alone.

Using the method of the present invention, a sample of the multi-phase fluid is isolated from the flow line and the components $Z_r$ and $Z_i$ of the complex impedance measured at one or more vertical positions $x_{(j)}$ against time as the fluid separates out into its constituent parts. This gives:

$$Z_r(x=x_{(j)}, t) = F'[C_{(i)}(x=x_{(j)}, t)]$$

$$Z_i(x=x_{(j)}, t) = G'[C_{(i)}(x=x_{(j)}, t)]$$

F' and G' are functions of the concentration $C_{(i)}$ of each phase of the fluid at the position $x_{(j)}$ as a function of time t.

The concentration of the various phases are determined from the volumes after separation. Thus at $t=0$ (uniform mixture in the isolated sample) the values of F' and G' can be straight forwardly deduced from the knowledge of the volumes after separation. At $t=T$ (complete separation) F' and G' are known from the conductivities and permittivities of the pure phases of the constituent parts of the fluid.

Values of F' and G' at intermediate times can be deduced from a model of the separation process, laboratory calibration, or interpolation between $t=0$ and $t=T$.

Using this information a calibration of Z against concentration can be produced for the multi-phase fluid. This is done by eliminating the time variable for the two sets of data.

FIG. 2 shows graphically how the method is implemented for a two phase fluid. FIGS. 2(a) to (c) show the concentration $C_1$ (t) of one of the phases as a function of the measurement location for $t=0$, $t=t$ and $t=T$. It can be seen that this value varies from the fully mixed concentration $C_m$ in FIG. 2(a) to the pure phase ($C_1=1$ and $C_2=0$) in FIG. 2(c) via an intermediate value in FIG. 2(b). For the purpose of this example the variation in concentration between the two phases at $t=t$ is approximated by a linear relationship over the mixed zone between the two separated phases. Other more complex models of this process can of course be used.

Figure 2A:
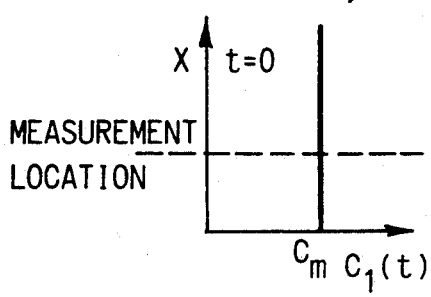
FIGS. 2a) to g) shows the basic measurements and method of the current invention.
Figure 2B:
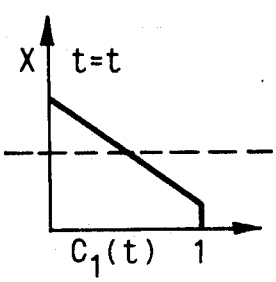
Figure 2C:
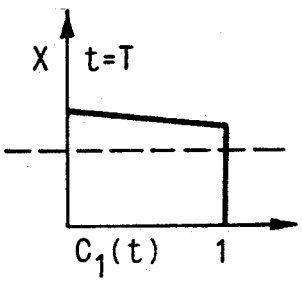
Figure 2D:
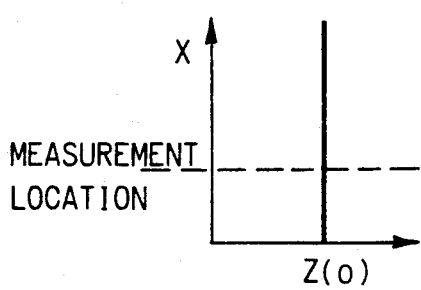
Figure 2E:
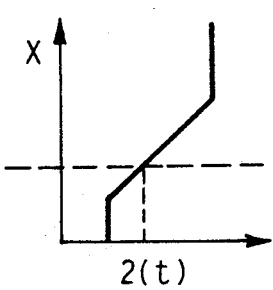
Figure 2F:
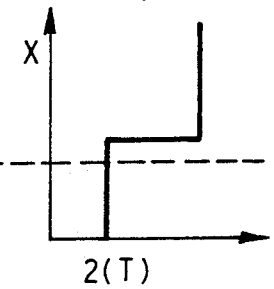

FIGS. 2(d) to (f) shows the value of impedance Z measured as a function of the same measurement location X at times corresponding to those for FIGS. 2(a) to (c) respectively. Thus it can be seen that the impedance varies from the values Z (0) to a value Z (T) via the intermediate value Z (t).

Figure 2G:
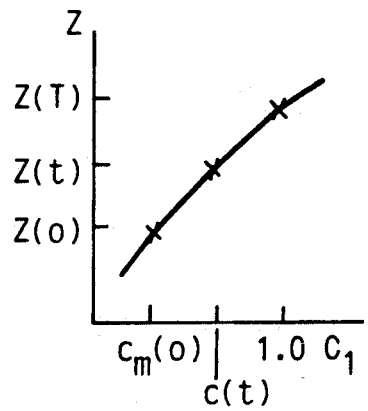

In FIG. 2(g) the concentration and impedance data from FIGS. 2(a) and (f) are brought together to give a calibration curve for Z in terms of concentration $C_1$ of a single one of the phases. Since we are considering a two phase system the calibration results in a simple curve. If, however, three or more phases are being considered then the result of the analysis will be at least a three dimensional calibration surface which cannot easily be shown in graphical form in this document.

Using this method results in a calibration which will always be very close to the actual values to be measured since it is made using a portion of the actual fluid being measured. Thus the calibration will not be affected by unexpected salt concentrations in the water or other variable factors since it will be made at line conditions.

Figure 3:
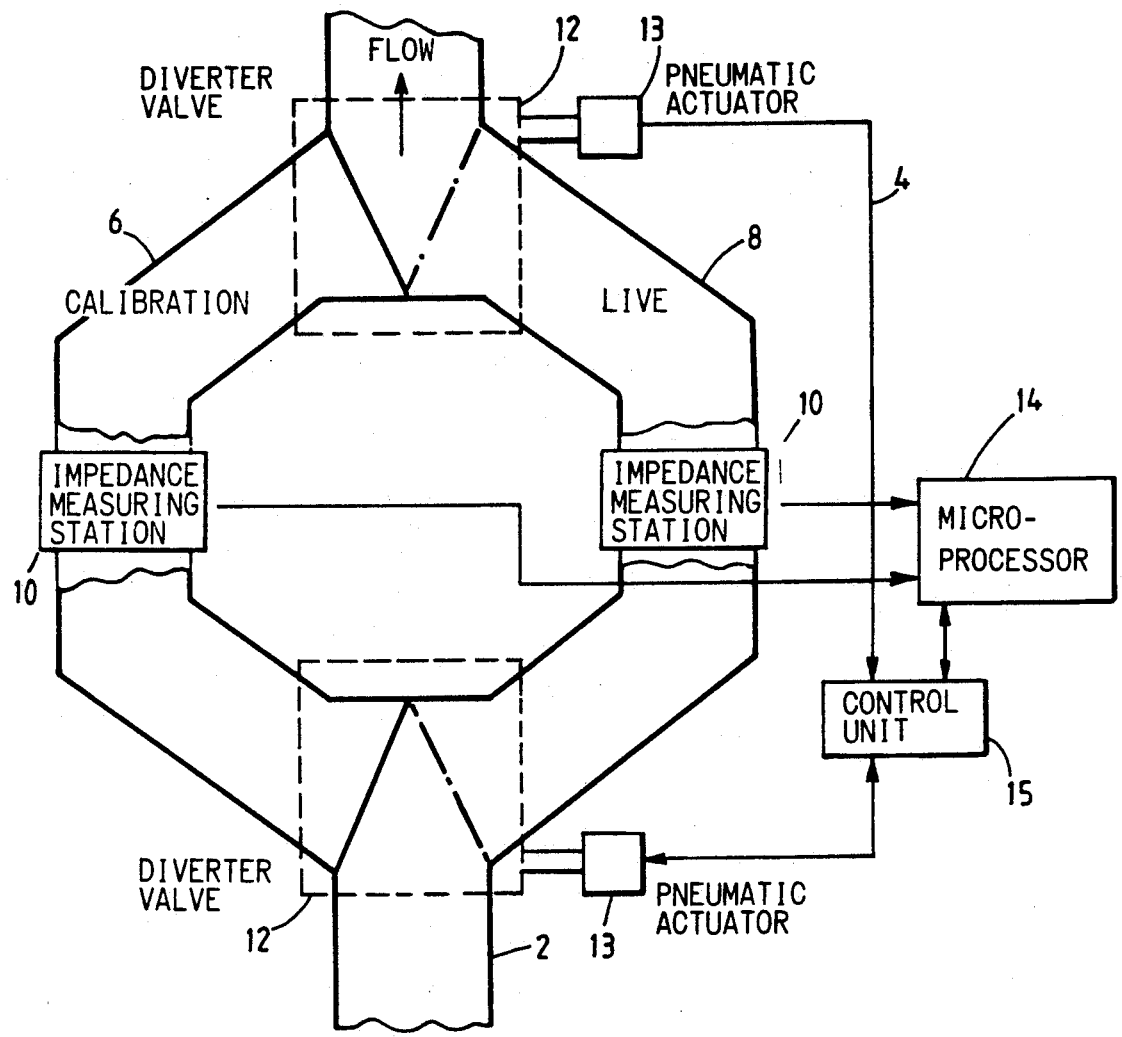
FIG. 3 shows a schematic diagram of an apparatus embodying the invention.

In order to obtain a sample of the fluid at line conditions it is necessary to be able to isolate a sample and this can be achieved using the apparatus provided by the present invention. A sampling/calibration system as shown in FIG. 3. In this, a multi-phase fluid flowing from an oil reservoir for examples is carried towards the surface in a pipe 2. Adjacent the exit from the well there is provided an impedance meter shown generally at 4. This comprises a first (calibration) passage 6 and a second (live) passage 8. Each of these passages includes a measuring station 10 at which the impedance of the fluid is measured.

The passages 6, 8 are connected to the pipe 2 by diverter valves 12. The valves 12 are operable to isolate one or another passage 6, 8 from the flow of fluid. In the present case, the first passage 6 is isolated such that the fluid contained therein is static. The fluid flows freely in the second passage 8. With the diverter valves 12 in the opposite position (shown in dotted line) the fluid flows through the first passage 6 and is isolated in the second passage 8. Thus a sample of the multi-phase fluid flowing through the passage 6 is isolated by moving the diverter valves 12 to the position shown.

Once the valves 12 have been closed as shown, the fluid trapped in the "calibration" passage 6 begins to separate into its constituent phases and measurements of the impedance are repeatedly taken at the measuring station 10. Once separation is complete the actual concentrations of the pure phases are determined and a calibration of impedance with respect to concentration produced according to the method described above.

Whilst this calibration of the instrumentation in passage 6 is taking place the fluid flowing from the reservoir is being monitored in the "live" passage 8. The calibration of the transducer in this was performed prior to the calibration of passage 6. Once passage 6 has been calibrated the valves 12 are moved to the position of the dotted lines and the instrumentation in passage 8 is recalibrated whilst the fluid flows through passage 6. This process is repeated thus ensuring that an up to date calibration is always available to monitor the impedance of the fluid.

In order to prevent any accidental closure of the flow route from the oil reservoir to the surface it is advisable to have the valves 12 ganged together so that they can only be moved simultaneously between the positions of the hard black lines and the dotted lines. This will prevent any blockage of flow through the apparatus 4.

The valves 12 are typically operated remotely by electro-mechanical or electro-pneumatic actuators 13. They can thus be electrically ganged together by providing simultaneous control signals to the actuators 13 from a control unit 15. Operation of the actuators 13 provides a trigger signal to a microprocessor 14 which causes it to take repeated sample measurements from the measuring station 10 in the calibration passage 6 whilst taking measurements of the actual fluid flowing in the line passage 8. The microprocessor 14 and control unit 15 may be provided integrally, the control unit functions all being implemented in the microprocessor.

The actuators are preferably of the type that provide indication signals as they move. This enables the control unit to halt movement of one valve if the other fails to move thus providing a safety system to prevent only one valve from moving.

Another consideration in the choice of valves is the speed of operation. Although the isolated samples does not have to be representative of the phase concentrations in the flowing fluid it is preferable that the fluid does not start to separate to any significant degree whilst the valves are closing the passage to isolate a sample of the fluid. The actual operation time required of the valves will depend on the meter size. A smaller meter will require faster operating valves. It will also depend on the actual fluid being measured since some multi-phase fluids separate out more quickly than others. A fluid which has a long separation time will not require such fast valves as those fluids with fast separation times.

Calibration of the closed passage 6 and monitoring of the live passage 8 is preferably done automatically by the microprocessor 14. This can be arranged to make measurements with the most recent calibration data available for a passage and provides these measurements to a user whilst simultaneously calibrating the other passage.

Figure 4:
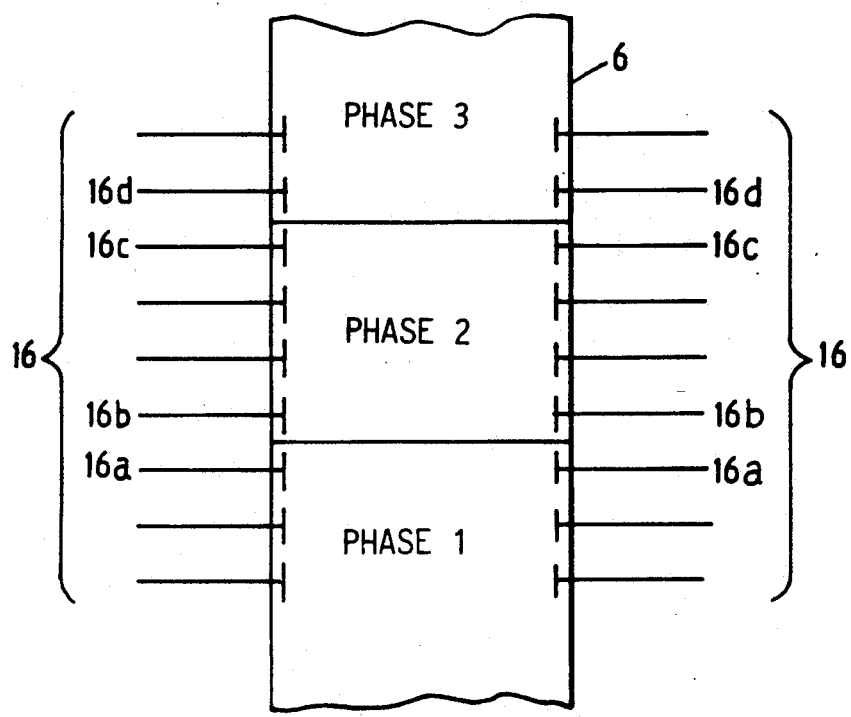
FIG. 4 shows apparatus for use in the meter of FIG. 3 to determine the concentrations of the phases of the fluids.

One problem encountered with an arrangement such as that shown in FIG. 3 is that when the apparatus is fitted at the mouth of an oil reservoir the proportions of the phases of the fluid after separation have to be determined remotely. One way of doing this is illustrated in FIG. 4. This shows the calibration passage 6 of FIG. 3. This passage is provided with a plurality of electrodes 16 which can be used to monitor impedance through the fluid in the passage. The passage is shown with a three phase fluid in its separated state. Where the phase changes between electrodes there will be a step change in the impedance measurement. Such a step change occurs between electrodes 16a and 16b and between 16c and 16d where the transitions from phase 1 to phase 2 and from phase 2 to phase 3 respectively occur. Thus a knowledge of the positions of the electrodes 16 and the impedance measurements will give a good estimate as to the relative concentrations of the three phases. The signals from the electrodes 16 can be supplied to the microprocessor 14 to determine the concentration.

In a preferred embodiment of the invention all the pairs of electrodes 16 shown in FIG. 4 would be calibrated whilst the passage 7 was isolated and thus when actually used to measure the impedance of the three phase flowing fluid an average figure could be derived from all the measurements.

It is clearly preferable in using the meter of FIG. 3 to mount it vertically so that the measuring station 10 is exposed to a range of concentration as the fluids separate. In practice it is possible to mount such a meter at any angle for which the separation of the phases can be monitored and meters could be specifically designed for horizontal mounting.

The fact that the meter is repeatedly recalibrated in line eliminates the errors caused by deposits which may build up on the electrodes as well as eliminating any offsets which might occur due to cabling positions during lab calibration. It also enables direct measurement to be made of the pure phase impedance at line conditions.

Figure 5:
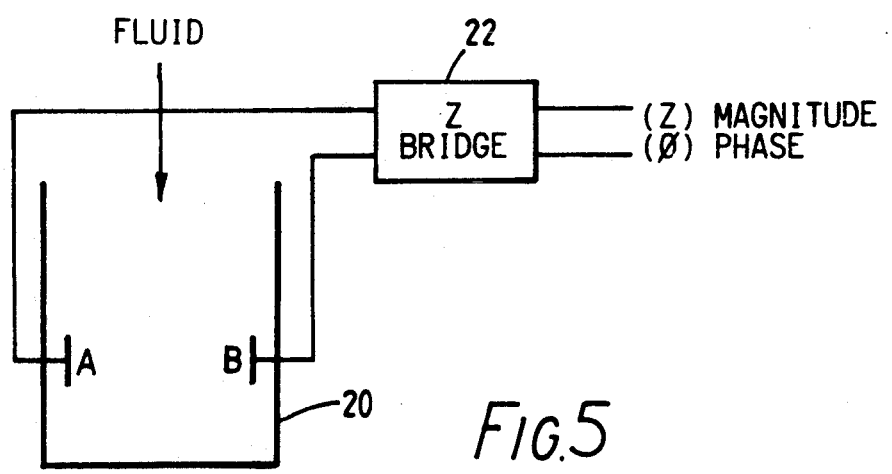
FIG. 5 shows an experimental arrangement to test the principles of the invention.

FIG. 5 shows an experimental arrangement in which the principle of operation of the calibration of the transducer has been tested. This comprises a jar which has been fitted with a pair of electrodes A and B on opposing sides and inside of the beaker. These two electrodes are coupled to an impedance bridge which monitors the magnitude of the impedance and the phase angle of the impedance. Thus giving the complex impedance.

Figure 6A:
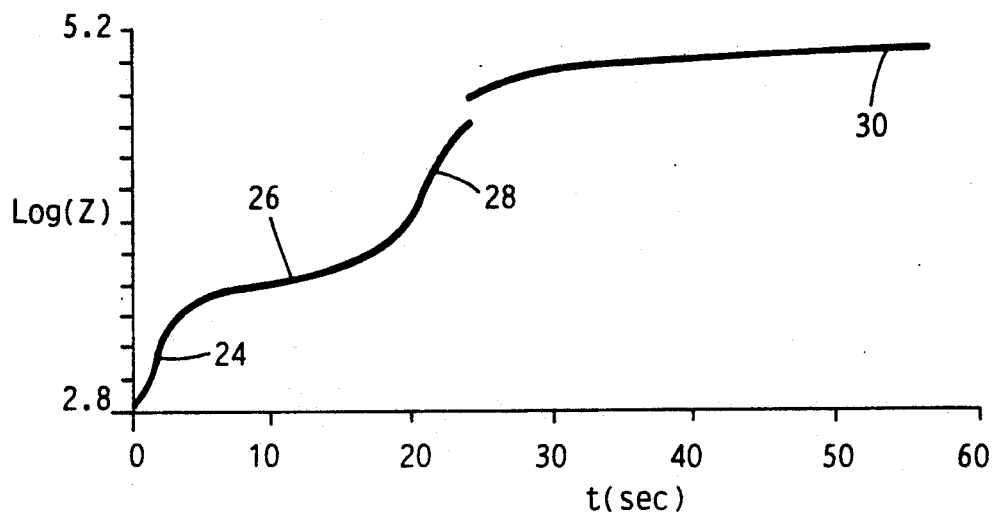
FIGS. 6a) and b) shows results obtained from the arrangement of FIG. 5.
Figure 6B:
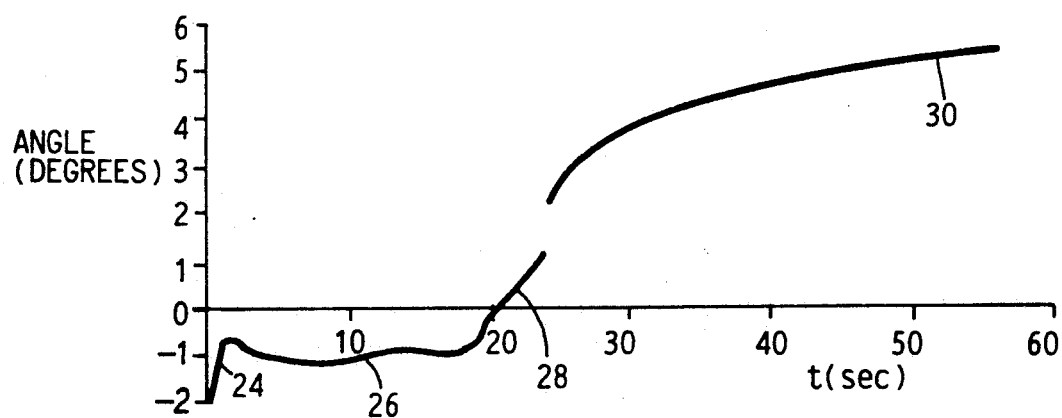

A mixture of oil, water and air is poured into the beaker 20 which effectively mixes the three phases. The mixture then separates out with time and the impedance is measured at regular intervals. The results of the log of the magnitude of the impedance and the phase angle with respect to time are shown in the graphs of FIG. 6a and FIG. 6b respectively. If it is assumed that at 0 seconds the three phases are evenly mixed it can be seen that there is an initial increase in the magnitude of the impedance at 24 and there is a corresponding jump in the phase angle at this point. There then follows a steady increase in the magnitude of the impedance accompanied by a fairly constant phase angle at 26. The magnitude of Z increases sharply at 28 and there is a corresponding step in the phase angle. The fluid then gradually reaches complete separation at 30. The shape of curves obtained depends upon the actual concentrations and on the position of the electrodes within the beaker.

The initial step 24 is caused by the air in the multiphase fluid rapidly separating out.

Another type of meter which can be adapted to the calibration method of the current invention is the gradiomanometer. Such a meter derives the density of a fluid from measurement of differential pressure along a section of pipe. Such a transducer is described in conjunction with a venturi meter in British Patent number GB 2,186,981.

Figure 7:
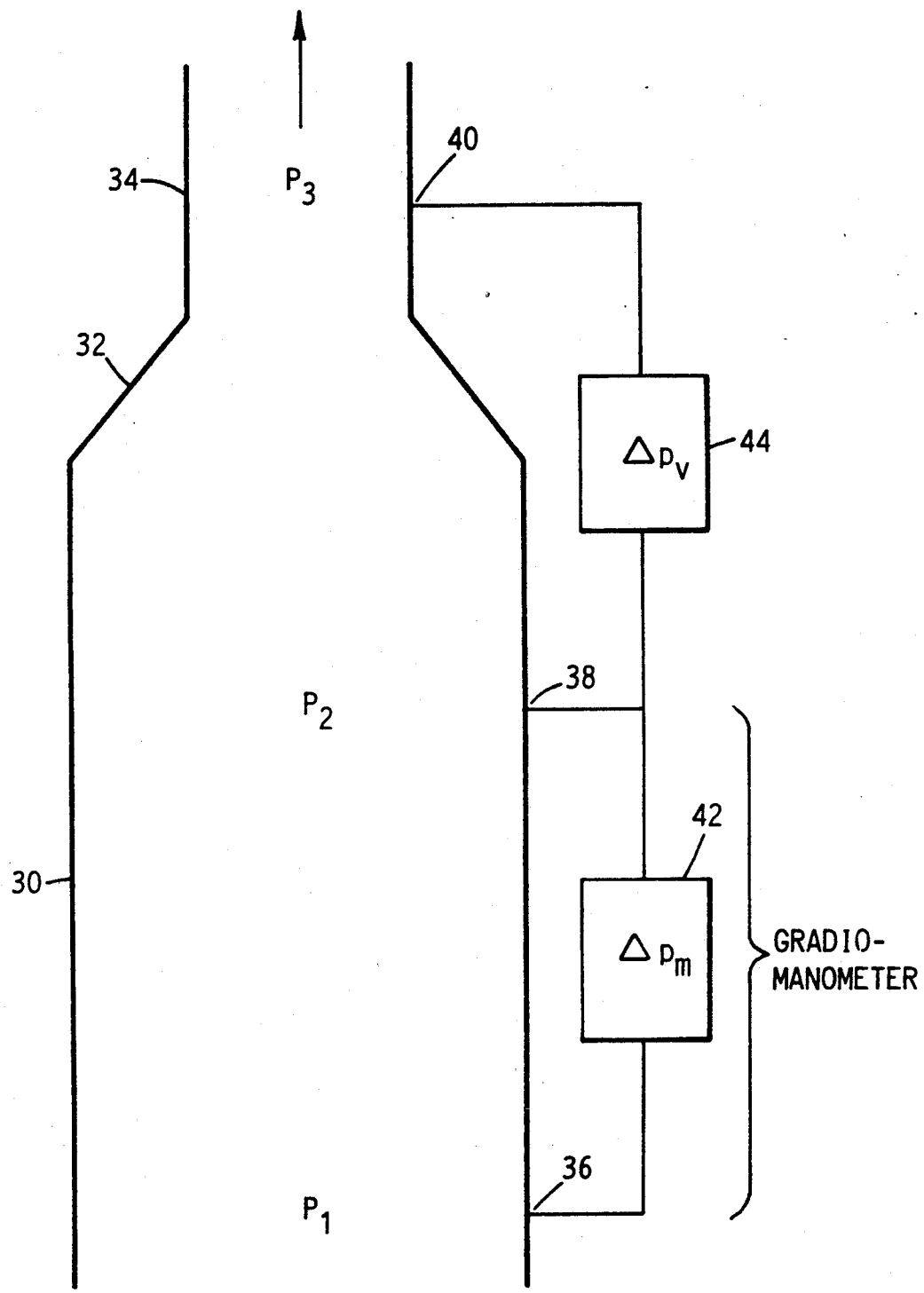
FIG. 7 shows a gradiomanometer/venturi meter which can be adapted to operate according to the present invention.

FIG. 7 shows a combined gradiomanometer and venturi meter of the type described in GB 2,186,981. This comprises a parallel section of pipe 30 which is the gradiomanometer portion. The venturi meter portion is comprised by a tapered section of pipe 32 followed by a further parallel section 34. Three pressure tappings 36, 38 and 40 are provided and they monitor pressures $P_1$, $P_2$ and $P_3$ respectively. A differential pressure transducer 42 monitors the difference between pressures $P_1$ and $P_2$ from tappings 36 and 38 and a further differential pressure transducer 44 monitors the difference between pressures $P_2$ and $P_3$.

In the gradiomanometer portion of FIG. 7 the density of the fluid flowing in the pipe is derived as a function of the differential pressure between pressure tappings 36 and 38, a friction factor, the distance between the pressure tappings and the angle of the gradiomanometer from vertical.

If the two passages 6 and 8 of the meter shown in FIG. 3 are instrumented as gradiomanometers then it is possible to use the transducer to find out the density of the pure phases of the liquid, their concentrations, and provide an estimate of the friction factor for fluid flowing in the pipe.

Figure 8:
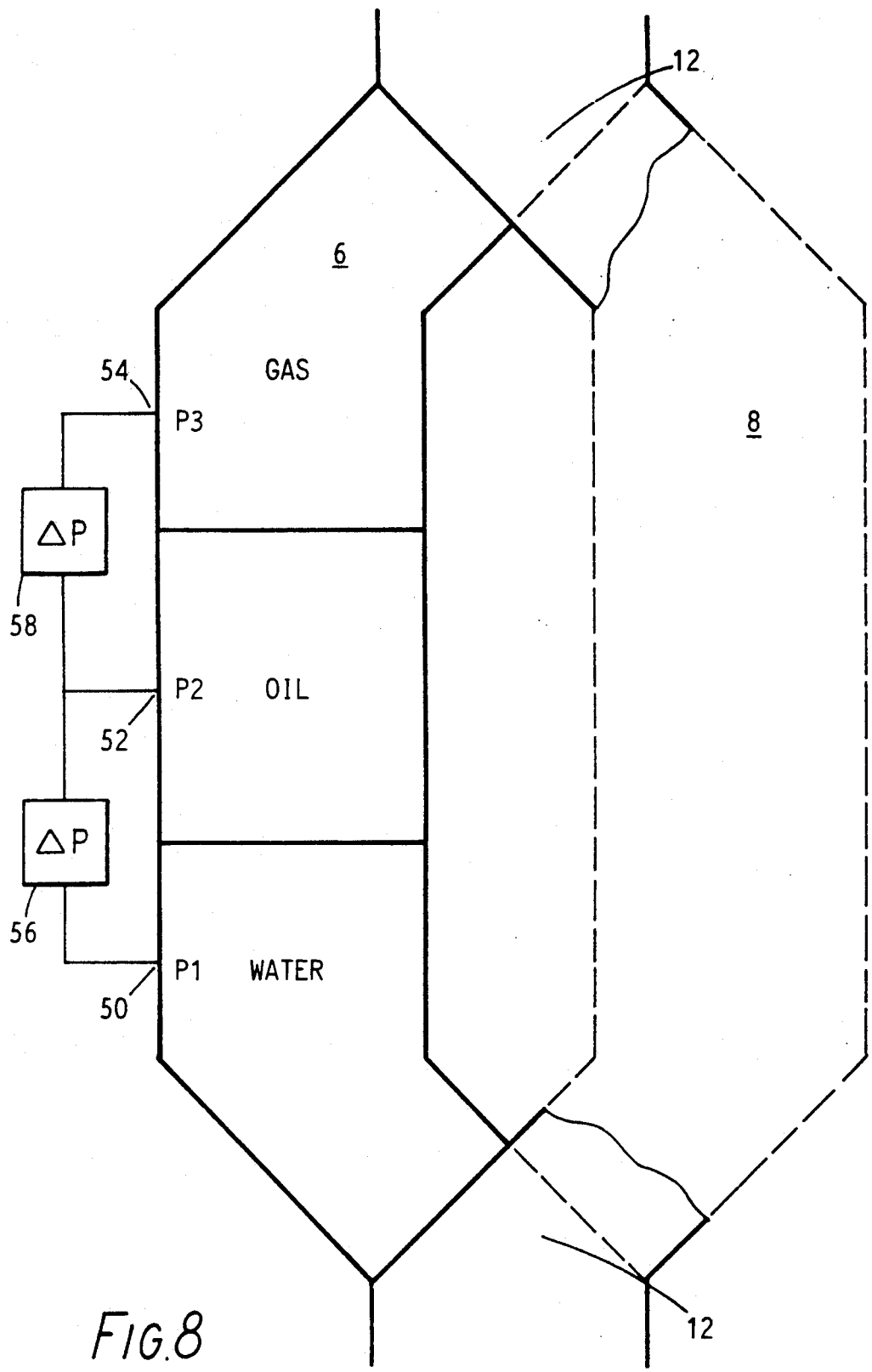
FIG. 8 shows a gradiomanometer adapted to operate in the meter shown in FIG. 3.

A gradiomanometer passage for use in the apparatus of FIG. 3 is shown in FIG. 8. The passage is shown with the valves (12) isolating the sample of fluid. The passage is provided with three pressure tappings 50, 52 and 54 which monitor pressures $P_1$, $P_2$ and $P_3$. Two differential pressure transducers 56, 58 monitor the pressure differences between $P_1$ and $P_2$ and between $P_2$ and $P_3$ respectively.

Once the three phase fluid shown in FIG. 8 has separated a knowledge of the positions of the transition from water to oil and from oil to gas and a knowledge of the differential pressure measurements combined with the position of the pressure tappings (50, 52 and 54) enables the densities of the water, oil and gas to be derived. It also provides a knowledge of the relative concentrations of the water, oil and gas phases. In FIG. 8 the differential pressure $P_2 - P_3$ gives a good approximation of the oil density, since the gas density is negligible compared to that of oil. The differential pressure $P_1 - P_2$ gives the oil/water density between 50 and 52. Knowing the oil density and the relative position of the oil/water interface, the water density is easily determined. However, it is preferable to have two pressure tappings in the same separated liquid phase. So, preferably the tappings 52 and 54 would be in the oil phase when separated so that the slight error otherwise caused by the gas can be neglected.

The positions of the transition from water to oil and from oil to gas could be monitored using a plurality of electrodes as shown in FIG. 4 and described above or alternatively by providing a large number of pressure tappings and detecting the positions of the transitions by looking for a significant change in differential pressure along the passage.

As the valves 12 close to isolate the sample of the single or multi-phase fluid in the passage the friction factor decreases as the velocity of the fluid flowing in the passage decreases. Pressure measurements made during this transitional period between maximum flow and no flow enable an estimate of the friction factor $F_m$ to be made. Alternatively, the friction factor can be determined from differential pressure measurement made with the fluid flowing and not flowing in the passage. Using this friction factor it is then possible to derive the density of the single phase fluid or the mean density of the fluid in the other passage of the transducer from the corresponding pressure tappings and differential pressure measurements.

When the valves 12 are closed, the density of the fluid in the calibration passage is determined, the friction factor being zero since the fluid does not move. In the live passage in which the fluid flows, the density measurement includes an effect from the friction factor. By comparing the two density measurements, a good estimate of the friction factor can be derived.

It is possible to use only one valve 12 and in such an arrangement this would be located at the upstream end of the meter. Although there would be interference due to fluid flowing past the open end of the passage this could be removed by averaging.

As with the impedance meter example the valves 12 are used to isolate first one passage and then the other of the meter thus enabling the pure phase densities and the friction factor to be regularly updated.

Meters using this invention benefit in that meter calibration is always being updated whilst data is being collected. Calibration is always made at line conditions e.g. pressure, temperature, etc, and a full calibration history of the meter is available. The calibration is made with any background electrical interference in place and thus does not suffer from errors which would occur due to differing electrical interference between a lab calibration and the in line position.

The type of meter to which the invention can be applied is not limited to an impedance meter or a gradiomanometer but can be any type of meter which measures a material property of a fluid, for example viscosity or surface tension.

Having two passages, live and calibration, allows measurements to continue to be made even if the instrumentation in one passage fails. In such a situation measurements are made with the fluid always flowing in the passage with the operational transducers. The calibration of the meter can no longer be done and hence the measurements cannot be guarantied to be so accurate. However, measurements can still be made whilst the faulty instrumentation is repaired.

Being able to measure the material properties of a fluid emerging from an oil well with the higher accuracy produced by the current invention enables a much better knowledge to be gained of an oil reservoir and thus enables total production from that reservoir to be optimised.

I claim:

1. Apparatus for measuring at least one property of a flowing multiphase fluid comprising:
   a) a pair of substantially parallel flow passages;
   b) means for directing said fluid into said flow passages;
   c) means for isolating at least one of said passages so as to prevent flow therethrough;
   d) a measuring point in each passage having at least one transducer connected thereto for measuring said at least one property of said fluid, the transducer in said at least one passage measuring said at least one property both when the fluid is flowing therethrough and when flow therethrough is prevented; and
   e) means for calculating, from a response of the transducer in said at least one passage when isolated, calibration data for the transducer when used to measure said at least one property in said flowing fluid.

2. Apparatus as claimed in claim 1, wherein respective end of said flow passages are connected to a pipe for said flowing fluid.

3. Apparatus as claimed in claim 2, wherein said isolating means comprise a pair of valves, one at each end of said passages, said valves being operable to selectively isolate one or other of said flow passages.

4. Apparatus as claimed in claim 3, wherein means are provided to operate said isolating means repeatedly to isolate periodically first one passage and then the other, such that measurement is made of said flowing fluid in the other passage while calibration is performed in the isolated passage.

5. Apparatus as claimed in claim 3, wherein means are provided to ensure that both valves operate to isolate the same passage.

6. Apparatus as claimed in claim 1, wherein means are provided for obtaining calibration data at a predetermined time after the passage is isolated.

7. Apparatus as claimed in claim 6, wherein said calculating means are arranged to receive data from each transducer on operation of said isolating means.

8. Apparatus as claimed in claim 1 for measuring at least one property of a multiphase fluid including means for determining the relative concentrations of the phases which separate in the isolated passage.

9. Apparatus as claimed in claim 8, wherein more than one transducer is provided in each passage.

10. Apparatus as claimed in claim 9, wherein the transducers are spaced along each passage.

11. Apparatus as claimed in claim 1 or 8, wherein said transducer comprises an impedance meter coupled to two electrodes at each measuring point.

12. Apparatus as claimed in claim 1, wherein each passage includes a differential pressure measurement device.

13. A method for measuring at least one property of a flowing multiphase fluid comprising:
   a) directing said fluid into a pair of substantially parallel flow passages;
   b) using at least one transducer provided at a measurement point in each passage to measure said at least one property;
   c) isolating one of said passages so as to prevent flow therethrough;
   d) measuring said at least one property in the isolated passage with said at least one transducer so as to obtain calibration data; and
   e) calibrating said at least one transducer from said calibration data.

14. A method as claimed in claim 13, wherein the isolating step is alternated between the passages.

15. A method as claimed in claim 13 or 14 for measuring at least one property of a flowing multiphase fluid, wherein measurements are made in the isolated passage until any phases present are fully separated.

16. A method as claimed in claim 15, wherein measurements are made on the pure phases after separation.

* * * * *